United States Patent [19]
Schobert et al.

[11] Patent Number: 5,406,611
[45] Date of Patent: Apr. 11, 1995

[54] MEDICAL X-RAY APPARATUS HAVING A GATING DEVICE

[75] Inventors: Erwin Schobert, Uttenreuth; Herbert Reisslein, Neunkirchen, both of Germany

[73] Assignee: Siemen Aktiengesellschaft, Munich, Germany

[21] Appl. No.: 86,660

[22] Filed: Jul. 6, 1993

[30] Foreign Application Priority Data

Aug. 13, 1992 [DE] Germany .................. 42 26 861.3

[51] Int. Cl.6 ............................................... G21K 1/04
[52] U.S. Cl. ............................................ 378/152; 378/150
[58] Field of Search ............................ 378/152, 150; 250/505.1

[56] References Cited
U.S. PATENT DOCUMENTS 3,187,179  6/1965  Craig et al. ................... 378/150
4,691,335  9/1987  Telorack .

FOREIGN PATENT DOCUMENTS 0336473  10/1989  European Pat. Off. .
1411312  10/1968  Germany .
3708505   9/1988  Germany .

OTHER PUBLICATIONS

"Bildgebende Systeme für die medizinische Diagnostik", Krestel (1980), pp. 334–335.
Patent Abstracts of Japan, P-856, vol. 13/No. 152 (Apr. 13, 1989) Japanese Application No. 62-150151.

Primary Examiner—Craig E. Church
Attorney, Agent, or Firm—Hill, Steadman & Simpson

[57] ABSTRACT

A gating device for a radiation apparatus has at least one diaphragm plate adjustable in the beam path of a radiation transmitter, the plate having at least one guide aligned obliquely relative to the longitudinal axis of the diaphragm plate and an adjustment mechanism is attached to the diaphragm plate for moving the diaphragm plate in a manner defined by its guide to adjust the position of the plate in the beam path.

10 Claims, 4 Drawing Sheets

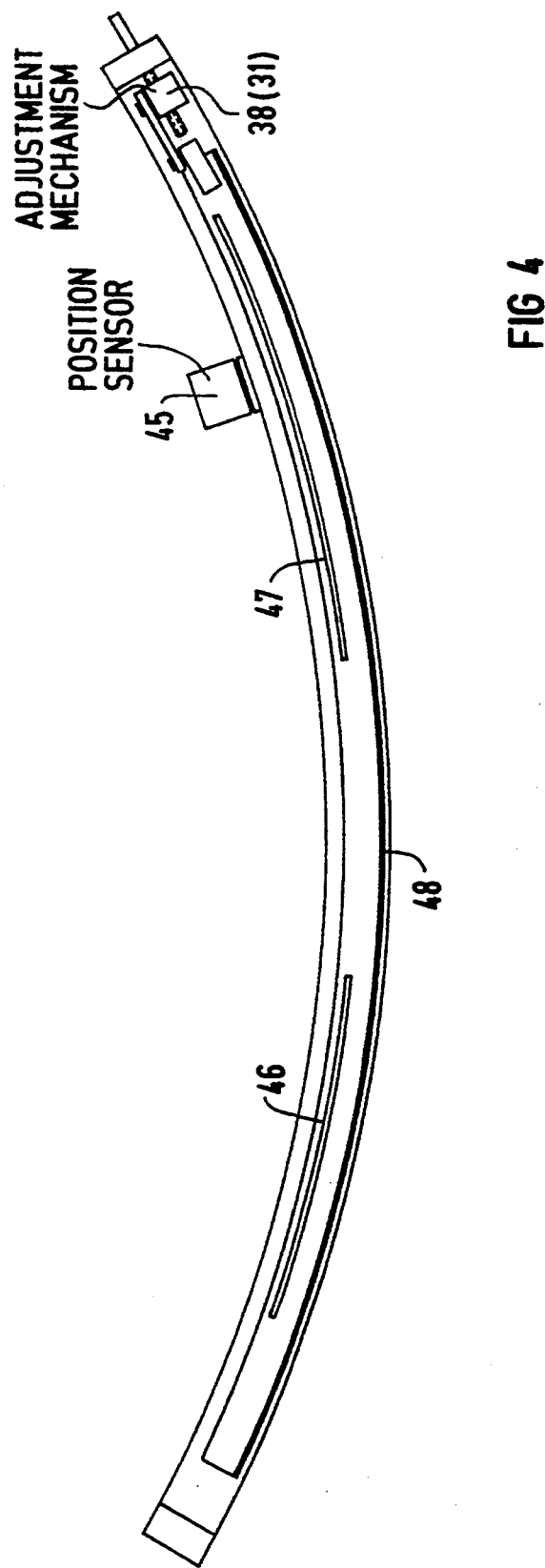

MEDICAL X-RAY APPARATUS HAVING A GATING DEVICE

BACKGROUND OF THE INVENTION

1. Field of the Invention

The present invention is directed to a radiation gating device, of the type suitable for use in an x-ray diagnostics installation.

2. Description of the Prior Art

German OS 1 441 312 discloses a gating device for an X-ray diagnostics installation which has two diaphragm plate pairs that are arranged offset by 90° relative to one another in parallel planes. The diaphragm plate pairs can be adjusted in opposite directions via their mounts, which are attached at the end-faces of the diaphragm plates.

The Siemens book "Bildgebende Systeme fuer die medizinische Diagnostik", edited by Erich Krestel, published by Siemens A. G., Berlin and Munich, 1980, pages 334 and 335, FIGS. 8.49 and 8.50 shows the beam path of a radiation apparatus in the form of a computer tomograph. The beam of the X-ray radiator is thereby gated to form a fan beam by a focus-proximate gating device and a gating device arranged in front of the arcuate radiation receiver composed of individual detectors. To that end, diaphragm plates arranged lying opposite one another form a slot-shaped opening that is variable via adjustment means. The adjustment of the diaphragm plate ensues in a direction perpendicular to its longitudinal axis, for which appropriate mounts and guides are provided. These mounts and guides are arranged at the end faces of the diaphragm plate aligned perpendicularly relative to the longitudinal axis of the diaphragm plate, so that a large structural width of the gating device is achieved. In order to accomplish the adjustment of the diaphragm plates, the adjustment means must be attached in the adjustment direction of the diaphragm plate, which results in a large structural width of the gating device and a mechanically complicated structure.

SUMMARY OF THE INVENTION

It is an object of the present invention to provide a radiation gating device having a compact structure and simple design, and which enables a precise adjustment of the diaphragm plate in the beam path.

This object is achieved in a radiation gating device constructed in accordance with the principles of the present invention having at least one diaphragm plate adjustable in the beam path of a radiation transmitter, with at least one guide aligned obliquely relative to the longitudinal axis of the diaphragm plate is provided at the diaphragm plate, and adjustment means attached to the diaphragm plate so that the diaphragm plate is adjustable in the beam path in a manner defined by the guide.

An advantage of the invention is that the adjustment means can be attached either along the longitudinal axis of the diaphragm plate or perpendicularly relative thereto, as a consequence of the guide extending obliquely relative to the longitudinal axis of the diaphragm plate, as a result of which the adjustment in the beam path can be effected. Only a single guide has to be provided for guiding the diaphragm plate, so that the structural outlay is low. The compact structure of the gating device derives in that the guide is provided at the diaphragm plate and not, as in the prior art, outside the edge region of the diaphragm plate.

A structure that is not complicated is achieved in an embodiment wherein the adjustment means if a motor-adjustable spindle that attached to the diaphragm plate via an articulation for the adjustment of the diaphragm plate.

In an embodiment which is uncomplicated in terms of fabrication technology, the guide is implemented as a recess provided in the diaphragm lamella into which, a pin, provided at the gating device housing, extends.

In an embodiment which is advantageous for obtaining a fan-shaped ray beam, two diaphragm plates are arranged opposite one another and form a slot-shaped opening for gating the beam of the radiation transmitter, and the diaphragm plates are adjustable at their guide arranged obliquely relative to the longitudinal axis of the diaphragm plates, so that the spacing of the diaphragm plates from one another can be increased or diminished.

Such a gating device can be especially advantageously utilized in a computer tomography apparatus when the gating device is arranged preceding the radiation receiver in the radiation direction. An economical format of the gating device thereby results because only a single adjustment means need be provided even if a plurality of diaphragm plates are arcuately joined to one another, with the adjustment means attached along the longitudinal axis of each diaphragm plate.

DESCRIPTION OF THE DRAWINGS

FIG. 4 shows the use of arcuately joined diaphragm plates in the gating device of FIG. 2.

DESCRIPTION OF THE PREFERRED EMBODIMENTS

Figure 1:
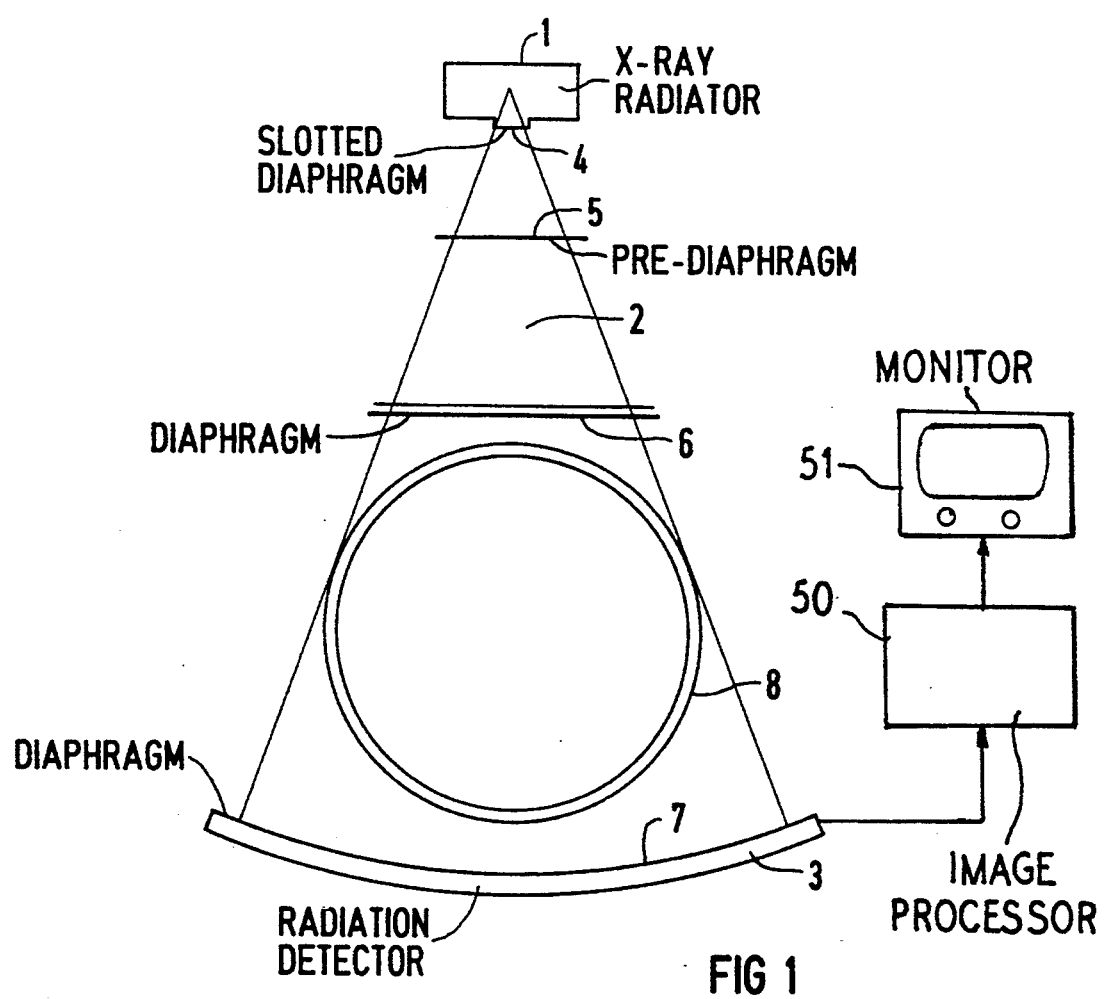
FIG. 1 is a schematic representation radiation apparatus in which a gating device constructed in accordance with the principles of the present invention can be employed.

FIG. 1 schematically shows a radiation apparatus in which the gating device disclosed herein can be used that, for example, is in the form of a computer tomography apparatus. In this radiation apparatus, an X-ray radiator 1 transmits an x-ray beam 2 to a radiation detector 3 that is arcuately fashioned and comprises individual detector elements adjoining one another. For gating the beam 2, a slotted diaphragm 4 is provided in the region of the X-ray radiator 1. A pre-diaphragm 5, a first diaphragm 6 and a second diaphragm 7 immediately in front of the radiation detector 3 for setting the slice widths are provided over the course of the further beam path.

In this radiation apparatus, the aforementioned arrangement rotates around a measurement field 8 in which an examination subject can be disposed. Dependent on the radiation penetrating through the examination subject, signals corresponding to the radiation intensity incident on the individual detectors are obtained at the respective outputs of the individual detectors. These signals are supplied to an image processor 50 whose output signals can be portrayed on a monitor 51 as an image of the examination subject.

Figure 2:
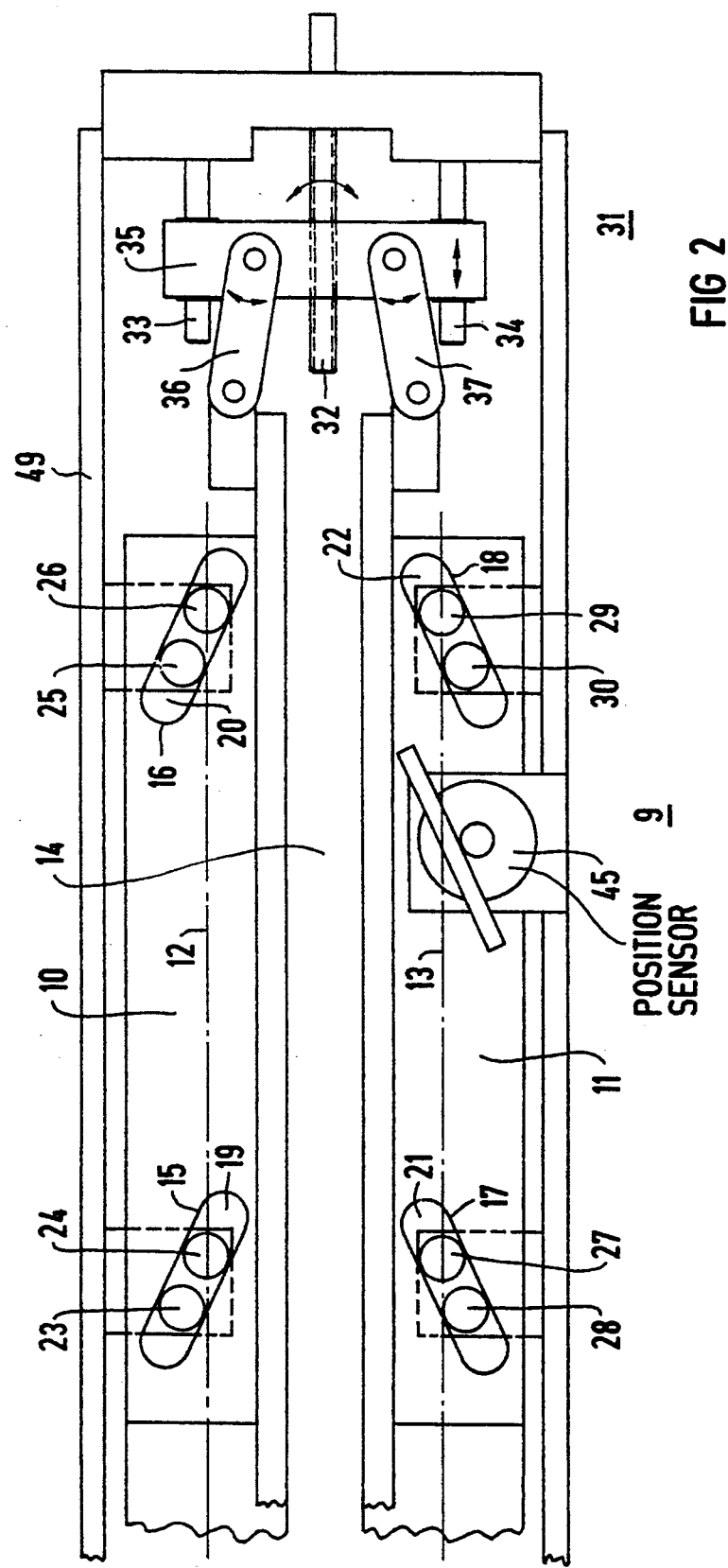
FIG. 2 is a plan view of a gating device constructed in accordance with the principles of the present invention, suitable for use in the radiation apparatus of FIG. 1.

FIG. 2 shows a gating device 9 of the invention in plan view for gating radiation from a radiation source, for example, the x-ray radiator 1. This gating device 9 has first and second diaphragm plates 10 and 11 having respective longitudinal axes 12 and 13 aligned parallel to one another, so that the first and second diaphragm plates 10 and 11 form a slot-shaped opening 14. Each diaphragm plate 10 and 11 has at least one guide. In the embodiment of FIG. 2, the plates 10 and 11 each have two guides, referenced 15 and 16, and 17 and 18.

In the exemplary embodiment, the guides 15 and 16 parallel to one another and are disposed obliquely relative to the longitudinal axis 12 as are the guides 17 and 18 relative to the longitudinal axis 13. The guides 15 and 16 are respectively formed by recesses 19 and 20 in the diaphragm plate 10 and first and second pin 23, 24 and 25, 26 respective engaging into the recesses 19 and 20. Similarly, the guides 17 and 18 are respectively formed by recesses 21 and 22 in the diaphragm plate 11 into which first and second pins 27, 28 and 29, 30 extend.

The diaphragm plates 10 and 11 can be adjusted especially easily at their guides 15, 16, 17 and 18 when the pins 23–30 are provided with a bearing implemented as, for example, a rolling bearing, whereby the bearing of each first pin 23, 25, 27 and 29 engages a long side of its recess 19, 20, 21, or 22 and the bearing of each second pin 24, 26, 28 and 30 engages the opposite long side of the same recess 19, 20, 21 or 22. The bearings can operate without play if eccentrically mounted on the pins 23–30. Within the context of the invention, the guides 15, 16, 17 and 18 can, of course, each be executed with only one pin, but are then less precise. The pins 23–30 are part of the housing 49 of the device 9.

Longitudinal movement of the first and second diaphragm plates 10 and 11 thus also causes the plates 10 and 11 to move in a direction perpendicular to their longitudinal axes 12 and 13 to make the slot-shaped opening 14 is larger or smaller. Such movement ensues with an adjustment mechanism 31. This adjustment mechanism 31 includes a threaded spindle 32 rotatable in a threaded bore or bushing of a carriage 35 movable on rails 33 and 34. One end of each of first and second articulations 36 and 37 is pivotally attached at the carriage 35; the other ends thereof are respectively connected to the first and second diaphragms plates 10 and 11. In the illustrated position, the diaphragm plates 10 and 11 are in a position in which a medium-sized slot-shaped opening 14 is established. When the slot-shaped opening 14 is to be enlarged, the spindle 32 is rotated around its longitudinal axis so that the carriage 35 is displaced toward the left in the plane of the drawing. The diaphragm plates 10 and 11 are thereby adjusted by the guides 15, 16, 17 and 18 via the first and second articulations 36 and 37, as a result of which the spacing between the diaphragm plates 10 and 11 increases.

The diaphragm plates 10 and 11 are thereby preferably adjusted simultaneously and symmetrically relative to the central longitudinal axis of the radiation receiver. Within the context of the invention, however, one diaphragm plate can be stationary, while the other diaphragm plate is adjustable for varying the slot-shaped opening 14. It is also possible that the guides of diaphragm plates arranged opposite one another exhibit a different pitch, so that the diaphragm plates are asymmetrically adjustable relative to the central longitudinal axis of the radiation receiver 3.

Dependent on the angle that the guides 15, 16, 17 and 18 describe relative to the longitudinal axes 12 and 13 and dependent on their lengths, the maximum spacing between the diaphragm plates 10 and 11 which can be achieved can be predetermined. If the angle becomes obtuse, then a high exertion of force is required for the adjustment of the diaphragm plates 10 and 11 and the precision with which a spacing can be set between the diaphragm plates 10 and 11 is low. With an acute angle, the adjustability of the first and second diaphragm plates 10 and 11 is facilitated and the precision with which a predetermined spacing of the diaphragm plates 10 and 11 can be set is high. It has proven advantageous when the guides 15, 16 17 and 18 describe an angle of approximately 15°–45°, preferably 25° relative to the respective longitudinal axis 12 and 13 of the diaphragm plates 10 and 11.

Within the context of the invention, the guide can be executed not only as a recess and pin but also as a channel into which a ridge (or web) engages. A ridge (or web) can also be provided with roller bearings.

Figure 3:
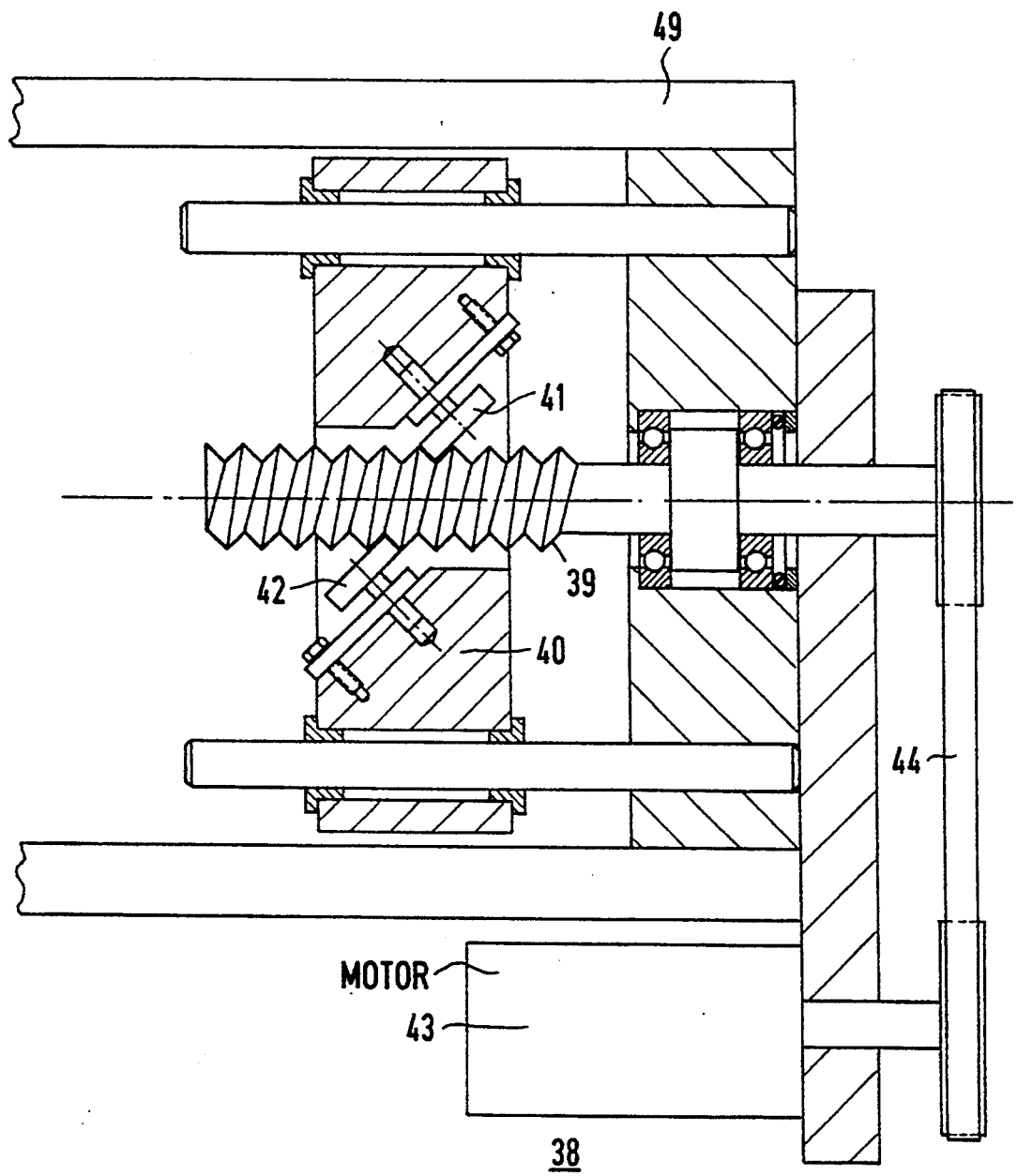
FIG. 3 is a sectional view of an adjustment means for the gating device according to FIG. 2.

FIG. 3 shows a preferred exemplary embodiment of an adjustment mechanism 38 for the first and second diaphragm plates 10 and 11. Differing from the above-described adjustment mechanism 31, wherein a threaded bushing or bore into which the spindle 32 extends must be provided at the carriage 35, the adjustment mechanism 38 of FIG. 3 has a spindle 39 having threads at a pitch such that bearing means held in the carriage 40 and preferably executed as a roller bearing 41 and 42 can engage the threads. The roller bearings 41 and 42 can be adjusted such via eccentric mounts such that no play occurs between the carriage 40 and the spindle 39. The first and second articulations 36 and 37 described with reference to FIG. 2 attach at the carriage 40 for adjusting the first and second diaphragm plates 10 and 11. Also shown in FIG. 3 is a motor 43, which can be a stepping motor or DC motor, is attached to the spindle 39, for example via a chain or via a toothed belt 44.

In addition to the absence of play in the bearings of the adjustment mechanism 38, it should be emphasized that it is extremely rugged and insensitive to dirt.

The spindle 32 according to FIG. 2 can, for example, be provided with a thread according to DIN13 as a commercially available spindle. In order to reduce the play between the carriage 35 and the spindle 32 (or the carriage 40 and the spindle 39) the spindle 32 or 39 can also be provided with a trapezoidal thread that engages a bushing of the carriage 35 (or 40) that is provided with a corresponding thread. The bushing can be executed as a nut. In order to reduce play, the bushing is axially divided and is prestressed via a spring element, for example a rubber ring. The bearing play is also considerably reduced as a result of this measure.

Adjustment of the diaphragm plates at their guides 15, 16, 17 and 18, can alternatively ensue via an adjustable eccentric attached to at least one of the diaphragm plates 10 and 11.

For identifying the position of the diaphragm plates 10 and 11, a position sensor 45 as shown in FIGS. 2 and 4 can be provided, such as an encoder, potentiometer or resolver.

When the gating device of the invention is to be utilized in a computer tomography apparatus and, in particular, as a diaphragm in front of the individual detector elements, then it is advantageous when, as shown in FIG. 4, a plurality of diaphragm plates 10 and 11 according to FIG. 2 adjoin one another and are fashioned arcuately. Due to the connection of the diaphragm plates 10 and 11 to one another, only one adjustment mechanism 31 or 38 is required via which the adjustment of the diaphragm plates 10 and 11 can ensue. The diaphragm plates can be entirely composed of a material having high radiation absorption.

Within the context of the invention, however, it is an alternative to provide diaphragm plates with carrier plates 46 and 47 composed, for example, of aluminum and having the guides described above, so that a material having high radiation absorption must be provided only in the region of one end face of each plate. When such diaphragm plates are to be arcuately joined to one another, preferably two or more carrier plates 46 and 47 are arranged at a distance from one another, joined to one another via a ring segment or a ring 48 composed of a material having high radiation absorption. The individual carrier plates 46 and 47 can include one or more guides as described above. An advantage of this embodiment is that the mass to be moved given an adjustment of the diaphragm plates is extremely low.

The described gating device, of course, can be utilized not only in a computer tomography apparatus but also in other radiation systems, for example, x-ray diagnostics installations, electron beam devices, radiation therapy devices and in light sources for gating the beam. The gating device can have only one diaphragm plate, or a plurality of diaphragm plates.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray apparatus comprising:
   means adapted for receiving a patient;
   an x-ray source which emits an x-ray beam directed at said patient for medical interaction with said patient;
   a gating device disposed in the path of said x-ray beam preceding said means adapted for receiving said patient, said gating device including a housing;
   first and second rectangular diaphragm plates in said housing consisting at least partially of x-ray opaque material and disposed at opposite sides of said x-ray beam, said diaphragm plates each having a longitudinal axis and at least one of said diaphragm plates having a recess therein extending obliquely relative to said longitudinal axis;
   means in said housing attached at one end of said at least one of said diaphragm plates for moving said at least one of said diaphragm plates along its longitudinal axis; and
   a guide pin attached to said housing and engaging said at least one diaphragm plate by projecting into said recess for causing said at least one diaphragm plate, when moved along its longitudinal axis, also to move within said x-ray beam in a direction perpendicular to its longitudinal axis.

2. An x-ray apparatus as claimed in claim 1 wherein said means for moving said one diaphragm plate along said longitudinal axis comprises:
   a carriage;
   a rotatable spindle threadably engaged in said carriage so that said carriage moves in opposite directions along said longitudinal axis dependent on the direction of rotation of said spindle; and
   an articulated mechanical connection between said one diaphragm plate and said carriage.

3. An x-ray apparatus as claimed in claim 2 wherein said carriage has a bore extending therethrough in which said spindle is disposed, and said carriage having roller bearings disposed in said bore and engaging threads of said spindle.

4. An x-ray apparatus as claimed in claim 1 comprising a plurality of first diaphragm plates corresponding to said first diaphragm plate and connected to form an arc and a plurality of second diaphragm plates corresponding to said second diaphragm plate and connected to form an arc.

5. An x-ray apparatus as claimed in claim 1 further comprising a rolling bearing carried on said guide pin and disposed to roll against said diaphragm plate as said diaphragm plate is moved along its longitudinal axis and perpendicular to its longitudinal axis.

6. An x-ray apparatus comprising:
   means adapted to receive a patient;
   an x-ray source with emits an x-ray beam directed at said patient;
   means for detecting x-rays attenuated by said patient and for generating electrical signals corresponding to the attenuated x-rays;
   means for generating an image of said patient from said electrical signals;
   a gating device disposed in the path of said x-ray beam preceding said means adapted for receiving a patient, said gating device including a housing;
   first and second rectangular diaphragm plates in said housing consisting at least partially of x-ray opaque material and disposed at opposite sides of said x-ray beam, said diaphragm plates each having a longitudinal axis and at least one of said diaphragm plates having a recess therein extending obliquely relative to its longitudinal axis;
   means in said housing attached at one end of said one diaphragm plate for moving said one diaphragm plate along its longitudinal axis; and
   a guide pin attached to said housing and engaging said one diaphragm plate by projecting into said recess for causing said one diaphragm plate, when moved along its longitudinal axis, also to move within said x-ray beam in a direction perpendicular to its longitudinal axis.

7. An x-ray apparatus as claimed in claim 6 wherein said means for moving said one diaphragm plate along its longitudinal axes comprises:
   a carriage;
   a rotatable spindle threadably engaged in said carriage so that said carriage moves in opposite directions along said longitudinal axis dependent on the direction of rotation of said spindle; and
   an articulated mechanical connection between said one diaphragm plate and said carriage.

8. A gating device as claimed in claim 7 wherein said carriage has a bore extending therethrough in which said spindle is disposed, and said carriage having roller bearings disposed in said bore and engaging threads of said spindle.

9. An x-ray apparatus as claimed in claim 6 further comprising a rolling bearing carried on said guide pin and disposed to roll against said diaphragm plate as said diaphragm plate is moved along its longitudinal axis and perpendicular to its longitudinal axis.

10. A gating device as claimed in claim 6 comprising a plurality of first diaphragm plates corresponding to said first diaphragm plate and connected to form an arc and a plurality of second diaphragm plates corresponding to said second diaphragm plate and connected to form an arc.

* * * * *